United States Patent
Mattai et al.

(10) Patent No.: US 6,805,855 B2
(45) Date of Patent: Oct. 19, 2004

(54) COOL AND DRY ANTIPERSPIRANT STICK

(75) Inventors: Jairajh Mattai, Piscataway, NJ (US);
Eric Guenin, Pennington, NJ (US);
Suman Chopra, Dayton, NJ (US);
Patricia Hall-Puzio, Succasunna, NJ (US); Rosemary Miano, Martinsville, NJ (US)

(73) Assignee: Colgate-Palmolive Company, NY, NY (US)

( * ) Notice: Subject to any disclaimer, the term of this patent is extended or adjusted under 35 U.S.C. 154(b) by 0 days.

(21) Appl. No.: 10/806,747

(22) Filed: Mar. 23, 2004

(65) Prior Publication Data

US 2004/0180013 A1 Sep. 16, 2004

Related U.S. Application Data

(63) Continuation of application No. 10/178,576, filed on Jun. 24, 2002, now abandoned.

(51) Int. Cl.$^7$ ............... A61K 7/32; A61K 31/74; A61K 7/00

(52) U.S. Cl. ............ 424/65; 424/78.02; 424/78.08; 424/400; 424/401

(58) Field of Search ............... 424/65, 78.02, 424/78.08, 400, 401

(56) References Cited

U.S. PATENT DOCUMENTS

| 4,661,476 A | 4/1987 | Lane et al. |
| 5,783,211 A | 7/1998 | Manzo et al. |

FOREIGN PATENT DOCUMENTS

| EP | 0974332 | 7/1999 |
| WO | WO 98/43605 | 10/1998 |
| WO | WO 00/62737 | 10/2000 |
| WO | WO 01/66078 | 9/2001 |
| WO | WO 01/74306 | 10/2001 |
| WO | WO 03/030854 | 4/2003 |

*Primary Examiner*—Shelley A. Dodson
(74) *Attorney, Agent, or Firm*—Rosemary Miano

(57) ABSTRACT

An antiperspirant and/or deodorant stick composition is disclosed comprising (a) 10–60 weight % of a volatile silicone such as cyclomethicone; (b) 2–30 weight % of a low melting point wax gelling agent (particularly stearyl alcohol); (c) 1–10 weight % of a high melting point wax (such as hydrogenated castor oil); (d) 0–15 weight % of an emollient which is different from (b) and (c); (e) 0.1–10 weight % of a superabsorbent powder with little or no tack upon wetting such as starch graft homopolymers and copolymers of poly(2-propenamide-co-2-propenioic acid) sodium salt; (f) 0–30 weight % of an antiperspirant active; (g) 0–1 weight % of a dimethicone copolyol; (h) 0.01–0.5 weight % of a selected cooling agent; and (i) 0–5 weight % (particularly 0.1–5 weight %) of a fragrance; wherein the ratio of cooling agent to superabsorbent polymer is in the range of 1:50–1:2.

13 Claims, No Drawings

COOL AND DRY ANTIPERSPIRANT STICK

This is a continuation of prior application Ser. No. 10/178,576 filed on Jun. 24, 2002, which application is now abandoned and is incorporated herein by reference.

FIELD OF THE INVENTION

This invention relates to antiperspirant stick products that provide superior cool and dry feeling even under stressful conditions. A related case is being filed on the same day as this case (Attorney docket number IR 6776), Serial Number not yet accorded.

BACKGROUND OF THE INVENTION

Various stick products are described in the art. U.S. Pat. No. 5,833,964 describes an antiperspirant stick with substantially no visible residue on the skin after drying and which uses a combination of silicone and non-silicone emollients with stearyl alcohol and hydrogenated castor oil as suggested gelling agents.

U.S. Pat. No. 5,531,986 teaches a low residue antiperspirant comprising dimethicone copolyol in combination with high melting point and low melting point waxes.

U.S. Pat. No. 5,972,319 discloses a reduced residue antiperspirant comprising non-volatile emollients that are not silicones and which have adsorption and desorption properties relative to the antiperspirant material sufficient to achieve the desired reduction in residue.

The use of water absorbent materials is described in U.S. Ser. No. 09/971,978, filed Oct. 5, 2001, entitled Underarm Gel Products With Water Lock Component.

A number of formulations have been used that include some type of cooling agent such as menthol or mixtures of menthol with other ingredients. WO 00/42983 to Johnson & Johnson describes a freshening cosmetic comprising 0.01–2 weight % menthol and 0.1–10 weight % menthyl lactate in a 1/1 to 1/10 ratio.

The cooling sensation is intensified by the presence of an aqueous phase or air flow. Thus, the presence of sweat in the underarm area may increase the cooling sensation to undesirable levels of coolness, and it has been a problem to control the type and amount of cooling in the underarm environment. It is an object of the present invention to create a composition that provides a controlled coolness in the underarm area so as to give preferred aesthetics.

BRIEF SUMMARY OF THE INVENTION

The incorporation of cooling agents such as L-menthol; menthyl lactate; menthone glycerine; menthone glycerin acetal; (−)-isopulegol, N-ethyl-5-methyl-2-(1-methylethyl)-cyclohexanecarboxamide; N-ethyl-p-menthane-3-carboxxamide; 4-methyl-3-(1-pyrrolidinyl)-2[5H]-furanone; N,2,3-trimethyl-2-isopropylbutanamide (also known as 2-isopropyl-N,2,3-trimethylbutyramide); menthoxypropanediol; methanediol; vanillyl butyl ether; in an underarm product in combination with a selected superabsorbent material provides a superior product that balances a cooling effect with a dry sensation to give a constant dry cool perception in the underarm area over an extended period of time. The superabsorbent material in powder form acts to minimize the perception of wetness and acts as a water/liquid reservoir for the activation of the cooling agent. Since the selected cooling agents are activated by the presence of water, it is important to control the ratios of cooling agent and superabsorbent powder to achieve the desired effect.

DETAILED DESCRIPTION OF THE INVENTION

This invention comprises an anhydrous, composition (no more than 1 weight % of added water (excluding any waters of hydration) which may optionally contain up to 5 weight % of a nonionic surfactant having a hydrophilic-lipophilic balance (HLB value) greater than 6. The compositions of the invention comprise:

(a) 10–60 weight % (particularly 25–37%) of a volatile silicone such as cyclomethicone;
(b) 2–30 weight % (particularly 18–22%) of a low melting point wax gelling agent (particularly stearyl alcohol);
(c) 1–10 weight % high melting point wax (particularly hydrogenated castor oil with a melting point of about 80 degrees);
(d) 0–15 weight % (particularly 1–10%) of an emollient which is different from (b) and (c) (for example, C12–15 alkyl benzoate or PEG-8 distearate) (for example, 4% of PEG-8 distearate);
(e) 0.1–10 weight % of a superabsorbent powder with little or no tack upon wetting such as, for example, a water lock superabsorbent polymer selected from the group consisting of starch graft homopolymers and copolymers of poly(2-propenamide-co-2-propenioic acid) sodium salt (for example, A180 from Grain Processing Corp., Muscatine, Iowa);
(f) 0–30 weight % (particularly 0.1–30 weight %) of an antiperspirant active (for example, 22% of AA ZG 7168 or 7167 (from Summit Research Labs, Huguenot, N.Y.) or AZZ 902 SUF from Reheis Inc. (Berkeley Heights, N.J.);
(g) 0–1 weight % (particularly 0.01–1 weight %) of a dimethicone copolyol (for example, Dow Corning DC5225C, 10% active from Dow Corning Corp., Midland, Mich.);
(h) 0.01–0.5 weight % of a cooling agent selected from the group consisting of L-menthol; menthyl lactate; menthone glycerine; menthone glycerin acetal; (−)-isopulegol, N-ethyl-5-methyl-2-(1-methylethyl)-cyclohexanecarboxamide; N-ethyl-p-menthane-3-carboxxamide; 4-methyl-3-(1-pyrrolidinyl)-2[5H]-furanone; N,2,3-trimethyl-2-isopropylbutanamide (also known as 2-isopropyl-N,2,3-trimethylbutyramide); menthoxypropanediol; methanediol; and vanillyl butyl ether; and
(i) 0–5 weight % (particularly 0.1–5 weight %) of a fragrance;

wherein the ratio of cooling agent to superabsorbent polymer is in the range of 1:50–1:2 (more particularly 1:10–1:2).

It should be noted that the ratio of cooling agent to superabsorbent is an important feature of this invention. It is a cooling moderator that allows sufficient water to be released to activate the cooling agent while maintaining sufficient dryness to prevent the cooling agent from feeling too wet.

The compositions of the invention may be made in the form of sticks, using techniques known in the art such as those described in U.S. Pat. Nos. 5,531,986; 5,833,964; and 5,972,319.

The compositions according to the present invention include both high melting point and low melting point waxes. The low melting point waxes have a melting point in the range of about 37 up to about 65 degrees C., and the high melting point waxes have a melting point in the range starting at 65 degrees C. and going up to about 102 degrees C., especially in the range of 65–80 degrees C.

Illustrative high-melting point waxes include beeswax, spermaceti, carnuba, baysberry, candulilla. Montan, ozokerite, ceresin, paraffin, petroleum waxes, castor wax, synthetic waxes such as Fisher-Tropsch waxes, microcrystalline waxes, ethylene glycol diesters, triglyceride (preferably C18–36) waxes, and ethylene/vinyl acetate copolymers, and mixtures thereof. Derivatized waxes such as hexanediol behenyl beeswax (from Koster Keunen), silicone waxes (such as stearoxytrimethylsilane such as DC 580 from Dow Corning), synthetic waxes (such as Syncrowax HGL-C (C18–36 mixed acid triglycerides from Croda) with a preferred melting point of 65–80 degrees C. can be used. Specific castor waxes illustratively include MP-80 and MP-70.

Low melting point waxes include fatty acids, fatty alcohols, fatty acid esters and fatty acid amides having fatty chains of 8–30 carbons, preferably 12–18 carbons. Mixtures may also be used. Examples include cetyl alcohol, palmitic acid, myristyl alcohol, stearyl alcohol, paraffin, cetyl stearate, cetyl palmitate, cetyl myristate, stearyl stearate and mixtures of the foregoing. Silicone waxes may also be used such as stearoxy dimethicone. A particular example of stearyl alcohol is Lanette 18 from Henkel Corp.

A silicone copolyol (especially dimethicone copolyol) may be used in an amount of 0.05–0.5 weight % (actives basis), particularly 0.1–0.2% and, more particularly, 0.1–0.15%.

In general, silicone copolyols useful in the present invention include copolyols of the following Formulae I and II. Formula I materials may be represented by:

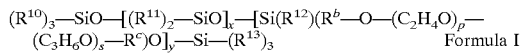

$(R^{10})_3$—SiO—[$(R^{11})_2$—SiO]$_x$—[Si($R^{12}$)($R^b$—O—$(C_2H_4O)_p$—$(C_3H_6O)_s$—$R^c$)O]$_y$—Si—$(R^{13})_3$   Formula I wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment —$(C_2H_4O)_p$—$(C_3H_6O)_s$— has a molecular weight in the range of 200 to 5,000; the segment preferably having fifty to one hundred mole percent of oxyethylene units —$(C_2H_4O)_p$— and one to fifty mole percent of oxypropylene units —$(C_3H_6O)_s$—; x has a value of 8 to 400; and y has a value of 2 to 40. Preferably each of $R^{10}$, $R^{11}$, $R^{12}$ and $R^{13}$ is a methyl group; $R^c$ is H; m is preferably three or four whereby the group $R^b$ is most preferably the radical —$(CH_2)_3$—; and the values of p and s are such as to provide a molecular weight of the oxyalkylene segment —$(C_2H_4O)_p$—$(C_3H_6O)_s$— of between about 1,000 to 3,000. Most preferably p and s should each have a value of about 18 to 28.

A second siloxane polyether (copolyol) has the Formula II:

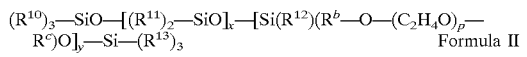

$(R^{10})_3$—SiO—[$(R^{11})_2$—SiO]$_x$—[Si($R^{12}$)($R^b$—O—$(C_2H_4O)_p$—$R^c$)O]$_y$—Si—$(R^{13})_3$   Formula II wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$ and $R^{13}$ substituents which are attached to the two terminal silicon atoms at the end of the siloxane chain can be substituted with the segment —$R^b$—O—$(C_2H_4O)_p$—$(C_3H_6O)_s$—$R^c$ or with the segment —$R^b$—O—$(C_2H_4O)_p$—$R^c$. In some instances, it may be desirable to provide the segment —$R^b$—O—$(C_2H_4O)_p$—$(C_3H_6O)_s$—$R^c$ or the segment —$R^b$—O—$(C_2H_4O)_p$—$R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING® 5225C from Dow Corning which is a 10% dimethicone copolyol in cyclomethicone; DOW CORNING® 2-5185C which is a 45–49% dimethicone copolyol in cyclomethicone; SILWET L-7622 from Witco; ABIL EM97 from Goldschmidt which is a 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING® 2-5185 material is of particular interest.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula III:

Formula III $$\begin{array}{l} CH_2-COOR^1 \\ | \\ CH-COOR^2 \\ | \\ CH_2-COOR^3 \end{array}$$

wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil, (b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4COOR^5$. The chain length for $R^4$ and $R^5$ can vary from 7 to 30 and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, neopentyl glycol dioctanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol, isoceteth-3 acetate, propylene glycol ceteth-3 acetate, octyldodecyl myristate, cetyl ricinoleate, myristyl myristate.

(d) saturated and unsaturated fatty acids which are the carboxylic acids obtained by hydrolysis of animal or vegetable fats and oils. These have general structure $R^6COOH$ with the $R^6$ group having a carbon chain length between 7 and 30; straight chain or branched. Specific examples include lauric, myristic, palmitic, stearic, oleic, linoleic and behenic acid.

(e) lanolin and its derivatives which are a complex esterified mixture of high molecular weight esters of (hydroxylated) fatty acids with aliphatic and alicyclic alcohols and sterols. General structures would include $R^8CH_2$—$(OCH_2CH_2)_nOH$ where $R^8$ represents the fatty groups derived from lanolin and n=5 to 75 or $R^9CO$—$(OCH_2CH_2)_nOH$ where $R^9CO$— represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.

(f) silicones and silanes the linear organo-substituted polysiloxanes which are polymers of silicon/oxygen with general structure:

(1) $(R^{10})_3SiO(Si(R^{11})_2O)_xSi(R^{12})_3$ where $R^{10}$, $R^{11}$ and $R^{12}$ can be the same or different and are each independently selected from the group consisting of phenyl and C1–C60 alkyl;

(2) $HO(R^{14})_2SiO(Si(R^{15})_2O)_xSi(R^{16})_2OH$, where $R^{14}$, $R^{15}$ and $R^{16}$ can be the same or different and are each independently selected from the group consisting of phenyl and C1–C60 alkyl; or (3) organo substituted silicon compounds of formula $R^{17}Si(R^{18})_2OSiR^{19}_3$ which are not polymeric where $R^{17}$, $R^{18}$ and $R^{19}$ can be the same or different and are each independently selected from the group consisting of phenyl and C1–C60 alkyl optionally with one or both of the terminal R groups also containing an hydroxyl group. Specific examples include dimethicone, dimethiconol behenate, $C_{30-45}$ alkyl methicone, stearoxytrimethylsilane, phenyl trimethicone and stearyl dimethicone.

(g) mixtures and blends of two or more of the foregoing.

Emollients of special interest include C12–15 alkyl benzoate (FINSOLV TN from Finetex Inc., Elmwood Park, N.J.), isopropyl myristate; and neopentyl glycol diheptanoate.

The emollient or emollient mixture or blend thereof incorporated in compositions according to the present invention can, illustratively, be included in amounts of 0.5–50%, preferably 1–25%, more preferably 3–12%, by weight, of the total weight of the composition.

The antiperspirant active can be selected from the group consisting of any of the known antiperspirant active materials. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Particular types of antiperspirant actives include aluminum zirconium trichlorohydrex and aluminum zirconium tetrachlorohydrex either with or without glycine. A particular antiperspirant active is aluminum trichlorohydrex gly such as AZZ-902 SUF (from Reheis Inc., Berkley Heights, N.J.) which has 95% of the particles less than 10 microns in size and AA ZG 7167 and AA ZG 7168 (from Summit Research Labs, Huguenot, N.Y.) which also has 95% of the particles less than 10 microns in size.

Another particular type of antiperspirant salt of interest is the group that has a low metal to chloride ratio such as in the range of 0.9–1.2:1. Examples of such salts are described in U.S. Pat. No. 6,375,937.

Antiperspirant actives can be incorporated into compositions according to the present invention in amounts in the range of 0.1–25% of the final composition, but the amount used will depend on the formulation of the composition. For example, at amounts in the lower end of the broader range (for example; 0.1–10% on an actives basis), a deodorant effect may be observed. At lower levels the antiperspirant active material will not substantially reduce the flow of perspiration, but will reduce malodor, for example, by acting as an antimicrobial material. At amounts of 10–25% (on an actives basis) such as 15–25%, by weight, of the total weight of the composition, an antiperspirant effect may be observed.

The antiperspirant active material is desirably included as particulate matter suspended in the composition of the present invention in amounts as described above, but can also be added as solutions or added directly to the mixture.

Desirably, the stick composition according to the present invention also includes inert filler materials and emollients, to improve cosmetic attributes. Such emollients illustratively include (but are not limited to) various ethoxylated/propoxylated surfactants, such as PPG-14 butyl ether.(e.g., Fluid AP by Union Carbide Corp.), or PEG-8-distearate mentioned previously, or mixtures of emollients some of which also have some surfactant character. The inert filler can be cornstarch, as mentioned previously, and/or talcum powder (magnesium silicate), fumed silica and/or inorganic clays, polyethylene, or mixtures of these inert particulate materials. Preferably, the inert filler, in particulate form, should have physical properties (e.g., size, shape, etc.) that are similar to those of the antiperspirant active material (e.g., antiperspirant active metal salt). Specific inert fillers and emollients have been described in the foregoing. However, inert fillers and/or emollients which can be incorporated in the stick compositions of the present invention are not limited to those specifically described in the foregoing, and can be others as known in the art, illustrated in U.S. patents previously referred to herein and incorporated by reference herein.

As mentioned previously, various known components of antiperspirant solid sticks can also be incorporated in the solid stick compositions according to the present invention, such known components including fragrances, bacteriostats, etc. Known bacteriostats include bacteriostatic quaternary ammonium compounds such as 2-amino-2-methyl-1-propanol (AMP), cetyl-trimethylammonium bromide, cetyl pyridinium, chloride, 2,4-4'-trichloro-2'-hydroxydiphenylether (Triclosan), etc., and various zinc salts. The bacteriostat can, illustratively, be included in the composition in an amount of 0.2–1.0% by weight, of the total weight of the composition.

The antiperspirant sticks of the present invention may be manufactured using methods known in the art. Typically, the ingredients are combined and heated to melt the components (other than the inert filler), and the melted components (together with particulate inert filler) are mixed. Desirably, volatile materials, such as the fragrance material, are incorporated in the composition in the latter stages of the mixing cycle, in order to avoid volatilization thereof. After mixing, the molten composition can be poured into stick-form molds (e.g., dispensing containers), as conventional in the art, after which the compositions harden into a solid.

The compositions according to the present invention can be utilized by the consumer, to reduce perspiration, as conventional antiperspirant solid stick compositions are used. An end of the molded composition can be elevated out of the dispensing container, so as to protrude out of the dispensing container, and rubbed against the skin in the axillary region, for example, so as to deposit antiperspirant active material in the axillary region, which prevents (or at least reduces) perspiration from the axillary region. Thus, by tubbing the composition of the present invention against the skin in regions of the body particularly prone to perspiration (for example, the axillary region), perspiration wetness in such regions can be controlled.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. The amounts of the components are in weight percents based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., $7^{th}$ ed., 1997).

Examples 1–6

Preparation of Stick

Cyclomethicone, C12–15 alkyl benzoate (Finsolv TN) and dimethicone copolyol (DC 5225C) are added to a beaker and heated to 70 degrees C. The stearyl alcohol is added and mixed at 70 degrees until melted using a Lightnin Blender (Model DS1010 from R. S. Engert & Co., Pensacola, Fla.) at 400 rpm. PEG-8 distearate is added at 75 degrees C. and mixed until melted. Hydrogenated castor oil is added and the mixture is heated to 80 degrees C. until melted. The mixture is cooled to 75 degrees and the antiperspirant active (AZZ 902 SUF from Reheis) is added slowly, keeping the temperature between 70–75 degrees C. The superabsorbent (A 180 from Grain Processing Corp.), if used, is now added. The mixture is stirred at 70–75 degrees C. for about 15 minutes and then cooled to 65 degrees C. The cooling agent/fragrance mixture is prepared by weighing L-Menthol and Menthyl lactate (Frescolat ML) (both obtained from Haarmann and Reimer Corp., Springfield, N.J.) into a small beaker, adding the fragrance and dissolving the solid menthol by gentle agitation at room temperature. The cooling agent/fragrance mixture is added to the reaction vessel at 65 degrees C. The mixture is cooled to 58–60 degrees C. and poured into suitable containers such as of the size and shape seen in stores for antiperspirant products. After the final mixture is poured into suitable containers, it is then passed through a cooling tunnel which is at about 4 degrees C. or placed in a refrigerator for a suitable length of time on a laboratory scale (about 15 minutes). Cooling is then completed at room temperature.

This process is repeated using the amounts of ingredients in Table A to make batches of about 400 grams as white opaque sticks. Amounts are in weight percent based on the total weight of the composition.

The antiperspirant active is AZZ 902 SUF.
The polyethylene is Microthene FN510 (Equistar).
The cyclomethicone is DC 345 (Dow Corning).
The superabsorbent is A180 (Grain Processing Corp.)

TABLE A

| Ingredient | #1 | #2 | #3 | #4 | #5 | #6 |
|---|---|---|---|---|---|---|
| Cyclomethicone | 30.80 | 25.80 | 31.30 | 26.30 | 28.30 | 28.80 |
| Stearyl alcohol | 20.00 | 20.00 | 20.00 | 20.00 | 20.00 | 20.00 |
| Finsolv TN | 12.00 | 12.00 | 12.00 | 12.00 | 12.00 | 12.00 |
| Superabsorbent | 0 | 5.00 | 0 | 5.00 | 2.50 | 2.50 |
| Hydrogenated castor oil (melting point - 80 degrees C.) | 4.00 | 4.00 | 4.00 | 4.00 | 4.00 | 4.00 |
| PEG-8 distearate | 4.00 | 4.00 | 4.00 | 4.00 | 4.00 | 4.00 |
| Antiperspirant active | 22.00 | 22.00 | 22.00 | 22.00 | 22.00 | 22.00 |

TABLE A-continued

| Ingredient | #1 | #2 | #3 | #4 | #5 | #6 |
|---|---|---|---|---|---|---|
| Dimethicone copolyol (DC 5225 C) | 5.00 | 5.00 | 5.00 | 5.00 | 5.00 | 5.00 |
| Fragrance | 1.20 | 1.20 | 1.20 | 1.20 | 1.20 | 1.20 |
| L-Menthol | 0.40 | 0.40 | 0.20 | 0.20 | 0.40 | 0.20 |
| Menthyl lactate | 0.60 | 0.60 | 0.30 | 0.30 | 0.60 | 0.30 |
| Total | 100 | 100 | 100 | 100 | 100 | 100 |

Examples 1 and 2

Evaluation of Properties

Stick compositions (300 gram samples) made according to Examples 1 (coolant but no superabsorbent and 2 (coolant and superabsorbent) were evaluated against each other. Approximately 0.5 gram of each sample was applied to both underarms of three test subjects. Cooling was evaluated on the basis of perception on a scale of 1 to 5 with 5 being the coolest. Dryness was also evaluated using a 1 to 5 rating with 5 being the driest. The products were evaluated 2 hours after application for each of two days. Examples 1 and 2 had approximately the same coolness rating, but Example 2 had a dryness rating that was more that twice that of Example 1 (4.00 vs. 1.67). This was true even though both Examples contained the same amount of antiperspirant active.

What is claimed is:

1. An antiperspirant and/or deodorant stick composition comprising:
   (a) 10–60 weight % of a volatile silicone;
   (b) 2–30 weight % of a low melting point wax gelling agent having a melting point in the range of about 37 degrees to about 65 degrees C.;
   (c) 1–10 weight % of a high melting point wax having a melting point in the range or 65–102 degrees C.;
   (d) 0–15 weight % of an emollient which is different from (b) and (c);
   (e) 0.1–10 weight % of a superabsorbent powder with little or no tack upon wetting;
   (f) 0–30 weight % of an antiperspirant active;
   (g) 0–1 weight of a dimethicone copolyol;
   (h) 0.01–0.5 weight % of a cooling agent selected from the group consisting of L-menthol; menthyl lactate; menthone glycerine; menthone glycerin acetal; (−)-isopulegol, N-ethyl-5-methyl-2-(1-methylethyl)-cyclohexanecarboxamide; N-ethyl-p-menthane-3-carboxzamide; 4-methyl-3-(1-pyrrolidinyl)-2[5H]-furanone; N,2,3-trimethyl-2-isopropylbutanamide; menthoxypropanediol; methanediol; and vanillyl butyl ether; and
   (i) 0–5 weight % of a fragrance;
   wherein the ratio of cooling agent to superabsorbent polymer is in the range of 1:50–1:2.

2. A composition according to claim 1 wherein the volatile silicone is cyclomethicone.

3. A composition according to claim 1 wherein the low melting point wax is selected from the group consisting of fatty acids, fatty alcohols, fatty acid esters and fatty acid amides having fatty chains of 8–30 carbons.

4. A composition according to claim 1 wherein the low melting point wax is selected from the group consisting of cetyl alcohol, palmitic acid, myristyl alcohol, stearyl alcohol, paraffin, cetyl stearate, cetyl palmitate, cetyl myristate, stearyl stearate and mixtures of the foregoing.

5. A composition according to claim 1 wherein the low melting point wax is a silicone wax.

6. A composition according to claim 1 wherein the high melting point wax is selected from the group consisting of beeswax, spermaceti, carnuba, baysberry, candulilla. Montan, ozokerite, ceresin, paraffin, petroleum waxes, castor wax, synthetic waxes, microcrystalline waxes, ethylene glycol diesters, triglycerides, ethylene/vinyl acetate copolymers, derivatized waxes, silicone waxes, synthetic waxes, and mixtures thereof.

7. A composition according to claim 6 wherein the high melting point wax has a melting point of 65–80 degrees C. and is selected from the group consisting of C18–36 mixed acid triglycerides and castor waxes.

8. A composition according to claim 1 comprising 0.1–30 weight % of the antiperspirant active.

9. A composition according to claim 1 comprising 0.01–1 weight % of the dimethicone copolyol.

10. A composition according to claim 1 wherein the cooling agent is L-menthol, menthyl lactate, or mixtures thereof.

11. A composition according to claim 1 wherein the superabsorbent polymer is a water lock superabsorbent polymer selected from the group consisting of starch graft homopolymers and copolymers of poly(2-propenamide-co-2-propenioic acid) sodium salt.

12. A composition according to claim 1 wherein the ratio of cooling agent to superabsorbent polymer is in the range of 1:10–1:2.

13. A composition according to claim 1 wherein the antiperspirant active is an aluminum zirconium salt with a low metal to chloride ratio in the range of 0.9–1.2:1.

* * * * *